(12) United States Patent
Carlsgaard et al.

(10) Patent No.: US 9,990,581 B2
(45) Date of Patent: Jun. 5, 2018

(54) INSULIN DOSAGE ASSESSMENT AND RECOMMENDATION SYSTEM

(75) Inventors: Peter B. Carlsgaard, Zionsville, IN (US); Christen Rees, Indianapolis, IN (US); Robin S. Wagner, Indianapolis, IN (US)

(73) Assignee: Roche Diabetes Care, Inc., Indianapolis, IN (US)

(*) Notice: Subject to any disclaimer, the term of this patent is extended or adjusted under 35 U.S.C. 154(b) by 798 days.

(21) Appl. No.: 13/546,447

(22) Filed: Jul. 11, 2012

(65) Prior Publication Data
US 2014/0019396 A1   Jan. 16, 2014

(51) Int. Cl.
*G06N 5/02* (2006.01)
*G06F 19/00* (2018.01)
*A61M 5/172* (2006.01)

(52) U.S. Cl.
CPC ............. *G06N 5/02* (2013.01); *A61M 5/1723* (2013.01); *G06F 19/345* (2013.01); *G06F 19/3468* (2013.01)

(58) Field of Classification Search
None
See application file for complete search history.

(56) References Cited

U.S. PATENT DOCUMENTS

| 7,404,796 | B2 | 7/2008 | Ginsberg |
| 2003/0216628 | A1 | 11/2003 | Bortz et al. |
| 2010/0198520 | A1 | 8/2010 | Breton et al. |
| 2011/0021898 | A1 | 1/2011 | Wei et al. |
| 2011/0208027 | A1 | 8/2011 | Wagner et al. |

OTHER PUBLICATIONS

Thorne, "Attitudes toward patient expertise in chronic illness," Intl J Nursing Studies, 37, 303-311, 2000.*
Hornsten, "Nurses' experiences of conflicting encounters in diabetes care," EDN Summer, 5(2), 64-69, 2008.*
DAFNE Study Group, "raining in flexible, intensive insulin management to enable dietary freedom in people with type 1 diabetes: dose adjustment for normal eating (DAFNE) randomised controlled trial," vol. 325, 6 pages, 2002.*

(Continued)

*Primary Examiner* — G. Steven Vanni
(74) *Attorney, Agent, or Firm* — Harness Dickey

(57) ABSTRACT

A computer-implemented method is presented for recommending insulin dosage adjustments for a patient having diabetes. The method includes: identifying a plurality of bolus events from patient data; grouping bolus events having a recommended bolus dosage substantially equivalent to the amount of administered insulin into a first subset of bolus events; determining a bolus outcome for each of the bolus events in the first subset of bolus events, where the bolus outcome is expressed in relation to a target range of blood glucose values and is selected from a group including above the target range, in the target range and below the target range; determining whether one of the bolus outcomes is predominant amongst the bolus events in the first subset of bolus events; and generating a recommendation pertaining to insulin dosage for the patient in response to a determination that one of the bolus outcomes is predominant.

13 Claims, 8 Drawing Sheets

(56) References Cited

OTHER PUBLICATIONS

Civan, "Understanding and Facilitating Patient Expertise Sharing," doctoral dissertation, University of Washington, 2009.*
Thorne, "Attitudes toward patient expertise in chronic illness," Int'l J Nursing Studies, v. 37(4), p. 303-311, 2000.*
Hörnsten, "Nurses' experiences of conflicting encounters in diabetes care," European Diabetes Nursing, v. 5(2), p. 64-69, 2008.*
DAFNE Study Group, "Training in flexible, intensive insulin management to enable dietary freedom in people with type 1 diabetes: dose adjustment for normal eating (DAFNE) randomised controlled trial," BMJ: British Med J, v. 325(7367), p. 746, 2002.*

* cited by examiner

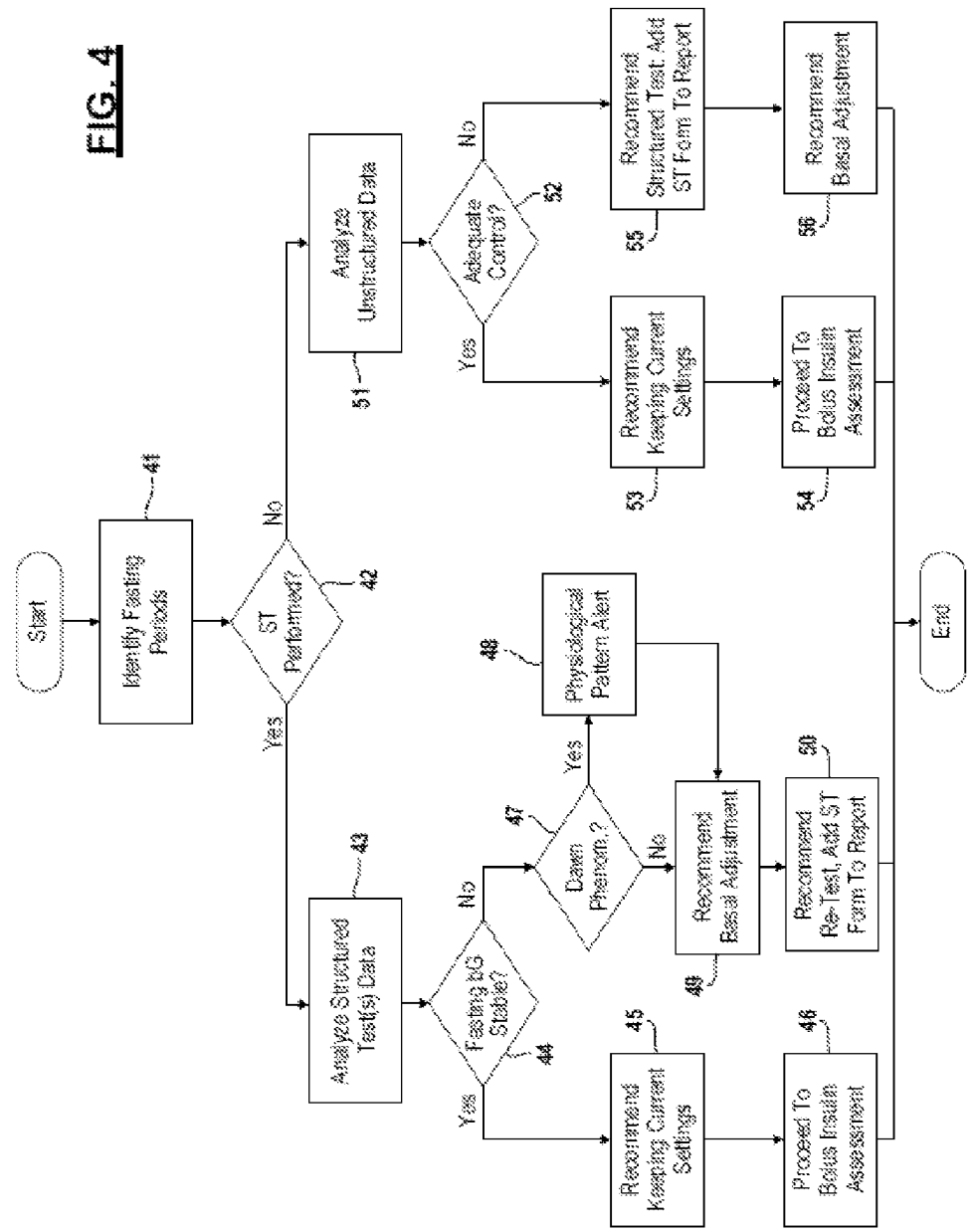

Insulin Therapy Report

Overview

| | |
|---|---|
| Mean Blood Glucose (bG): | 162 (mg/dL) +/- 77 |
| Hypoglycemic Events: | 10.1% of measurements indicate hypoglycemia |
| # Days | 81 days in record |

Basal (Long-Acting) Insulin

While there is no structured data available, as a whole the blood glucose record shows poor glycemic control for both waking and pre-meal fasting bG.

Structured testing strongly recommended. Begin with the Overnight Basal Structured Test then proceed to Daytime Basal.

Considering the number and severity of out-of-target bG readings, hypoglycemia is the greatest hazard. Decreasing background insulin at this time may minimize glycemic hazard.

Bolus (Short/Rapid-Acting) Insulin

Bolus insulin is taken at mealtimes and to correct high blood glucose readings. It is calculated using the I:CHO and ISF ratios. Once a stable basal rate has been established, the bolus insulin can be optimized, and adjusting these ratios can help do this.

Records do not show a structured test being performed during this time block. Structured tests are the most powerful tool for making therapy decisions. Any conclusions will draw from the overall record for now.

| | Below Target | In Target | Above Target | Not Followed Up |
|---|---|---|---|---|
| All | 19 (14.6%) | 46 (35.4%) | 65 (50.0%) | 166 (56.1%) |
| Meal | 19 (16.2%) | 40 (34.2%) | 58 (49.6%) | 138 (54.1%) |
| Correction | 0 (0.0%) | 6 (46.2%) | 7 (53.8%) | 28 (68.3%) |
| Rules Followed | 18 (15.1%) | 40 (33.6%) | 61 (51.3%) | 141 (54.2%) |
| Rules Not Followed | 1 (9.1%) | 6 (54.5%) | 4 (36.4%) | 25 (69.4%) |

Looking at both the frequency and severity out-of-target bolus outcomes, overall control may be improved by decreasing bolus insulin. Decreasing the insulin component of either I:CHO or ISF may help accomplish this. Complete a structured test to further help guide your adjustments.
Correction boluses (given without food) are the best indicator of whether ISF is correct. If there are enough correction boluses with a follow-up bG reading, these can help guide adjusting of ISF.

Accuracy in correction boluses need to be improved. Based on what is on record, increasing the insulin component of ISF may help improve accuracy. Performing a structured test will provide the best information for making this adjustment.
Dosing rules were generally followed. Try to identify specific circumstances that lead to the few times where they were not followed.

Modifying the insulin dose rules did not result in good control. Focus on optimizing and following therapy settings for dosing.

FIG. 8

INSULIN DOSAGE ASSESSMENT AND RECOMMENDATION SYSTEM

FIELD

The present disclosure relates to methods for assessing insulin dosages in patients with diabetes and providing recommendations regarding the same.

BACKGROUND

Diabetes mellitus, often referred to as diabetes, is a chronic condition in which a person has elevated blood glucose levels that result from defects in the body's ability to produce and/or use insulin. For people with diabetes, successful management requires monitoring the effects lifestyle changes can have in both short-term and long-term time frames. Regular testing of their blood glucose level can be an important part of diabetes management as a way to track changes throughout the day. For example, portable handheld medical diagnostic devices are often employed to measure concentrations of biologically significant components of bodily fluids, such as, for example, glucose concentration in blood. To test glucose with a glucose meter, a small sample of blood may be placed on a disposable test strip. The portable handheld glucose meter may include a strip port that receives the disposable test strip. The test strip may be coated with chemicals (glucose oxidase, dehydrogenase, or hexokinase) that combine with glucose in blood allowing it to measure the concentration of glucose in the blood sample. The portable handheld glucose meter then displays the glucose concentration as a number (or glucose measurement value). As a result, the portable handheld medical diagnostic devices and their accessories may work together to measure the amount of glucose in blood and be used to monitor glucose levels in one's home, healthcare facility or other location, for example, by persons having diabetes or by a healthcare professional.

Patients and their healthcare professionals may thereby track and analyze glucose measurements over a period of time to assess changes in the patient over the course of a day, week or other desirable timeframe. Healthcare professionals may in turn recommend a therapeutic regimen for the person having diabetes. The regimen may provide advice on eating, exercise and so forth with the goal of keeping the person's blood glucose within a target range similar to normal physiological concentration. In many instances, the regimen will also include prescribed insulin dosages. These doses may be composed of both basal insulin for baseline glucose metabolism and bolus insulin for blood glucose correction and/or mealtime glucose metabolism. Since many factors may affect the blood glucose level of a person, it may be helpful to periodically review the history of the person's blood glucose level and adjust prescribed insulin dosages. Accordingly, it is desirable to provide methods for recommending insulin dosage adjustment for patients having diabetes. This section provides background information related to the present disclosure which is not necessarily prior art.

SUMMARY

In one aspect the present disclosure, a computer-implemented method is presented for recommending insulin dosage adjustments for a patient having diabetes. The method includes: receiving patient data pertaining to diabetes care of the patient; identifying a plurality of bolus (rapid-acting insulin injection) events from the patient data, each of the identified bolus events having associated therewith a bolus dosage of insulin recommended to the patient, an amount of insulin administered to the patient in response to the recommended bolus dosage, and a blood glucose measure taken during an acting time of the administered insulin; grouping bolus events having a recommended bolus dosage substantially equivalent to the amount of administered insulin into a first subset of bolus events; determining a bolus outcome for each of the bolus events in the first subset of bolus events, where the bolus outcome is expressed in relation to a target range of blood glucose values and is selected from a group including above the target range, in the target range and below the target range; determining whether one of the bolus outcomes is predominant amongst the bolus events in the first subset of bolus events; and generating a recommendation pertaining to insulin dosage for the patient in response to a determination that one of the bolus outcomes is predominant.

In one implementation, which bolus outcome is predominant is determined by calculating a percentage of bolus outcomes in each grouping of bolus outcomes in relation to a number of bolus events in the first subset of bolus events. A given group of bolus outcomes is deemed predominant when the percentage of the given group of bolus outcomes exceeds a predefined threshold.

When the first subset of bolus events is predominantly in the target range of blood glucose values, the recommendation may be to maintain current insulin dosage.

When the first subset of bolus events is predominantly above the target range of blood glucose values, the recommendation may be to increase in insulin dosage.

When the first subset of bolus events is predominantly below the target range of blood glucose values, the recommendation may be to decrease insulin dosage.

When the first subset of bolus events are predominantly outside the target range of blood glucose values, the recommendation may be to acquire blood glucose measures from the patient in accordance with a structured collection procedure, where the structured collection procedure specifies timing for one or more collection events for obtaining blood glucose measures from the patient.

In another aspect of the disclosure, the computer-implemented method may evaluate basal insulin dosages before evaluating bolus insulin therapy. To do so, the method includes: identifying a plurality of fasting periods from the patient data, each of the identified fasting periods having associated therewith a starting blood glucose measure taken proximate to a start of the fasting period, an ending blood glucose measure taken proximate to an end of the fasting period and at least one intermediate blood glucose measure taken between the starting blood glucose measure and the ending blood glucose measure; determining a basal outcome for each of the fasting periods in the plurality of fasting periods, where the basal outcome is expressed in relation to a target range of blood glucose values and selected from a group including above the target range, in the target range and below the target range; determining whether one of the basal outcomes is predominant amongst the fasting periods in the plurality of fasting periods; and evaluating a bolus dosage of insulin prescribed for the patient in response to a determination that basal outcomes for the patient are predominantly in the target range of blood glucose values.

When basal outcomes are predominantly in the target range of blood glucose values, the recommendation may be to maintain current insulin dosage.

When basal outcomes are predominantly above the target range of blood glucose values, the recommendation may be to increase in insulin dosage.

When basal outcomes are predominantly below the target range of blood glucose values, the recommendation may be to decrease the insulin dosage.

When basal outcomes are predominantly outside the target range of blood glucose values, the recommendation may be to acquire blood glucose measures from the patient in accordance with a structured collection procedure, where the structured collection procedure specifies timing for one or more collection events for obtaining blood glucose measures from the patient.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

BRIEF DESCRIPTION OF THE DRAWINGS

FIG. 4 is a flowchart depicting an exemplary process for evaluating basal insulin dosages;

FIG. 8 is a drawing depicting an exemplary report provided to a user of the therapy advice tool.

Figure 1:
FIG. 1 is a drawing depicting a patient and a treating clinician.

The drawings described herein are for illustrative purposes only of selected embodiments and not all possible implementations, and are not intended to limits the scope of the present disclosure. Corresponding reference numerals indicate corresponding parts throughout the several views of the drawings.

DETAILED DESCRIPTION

Referring to FIG. 1, a person 10 with diabetes and a healthcare professional 12 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician. While this disclosure makes reference to diabetes care, it is readily understood that the concepts related to structured testing disclosed herein can be applied to other types of chronic diseases. Likewise, this disclosure makes reference to blood glucose measures but the concepts are extendable to other types of biomarker of a patient including but not limited to an interstitial glucose value, an HbA1c value, a heart rate measurement, a blood pressure measurement, lipids, triglycerides, cholesterol and the like.

During a healthcare consultation, the patient 10 typically shares with the clinician 12 a variety of patient data including blood glucose measurements, continuous glucose monitor data, amounts of insulin infused, amounts of food and beverages consumed, exercise schedules, and other lifestyle information. The clinician 12 may obtain additional patient data that includes measurements of HbA1C, cholesterol levels, triglycerides, blood pressure, and weight of the patient 10. The patient data can be recorded manually or electronically on a handheld diabetes management device 14, a diabetes analysis software executed on a personal computer (PC) 16, and/or a web-based diabetes analysis site (not shown). The clinician 12 can analyze the patient data manually or electronically using the diabetes analysis software and/or the web-based diabetes analysis site. After analyzing the patient data and reviewing adherence of the patient 10 to previously prescribed therapy, the clinician 12 can decide whether to modify the therapy for the patient 10.

Figure 2:
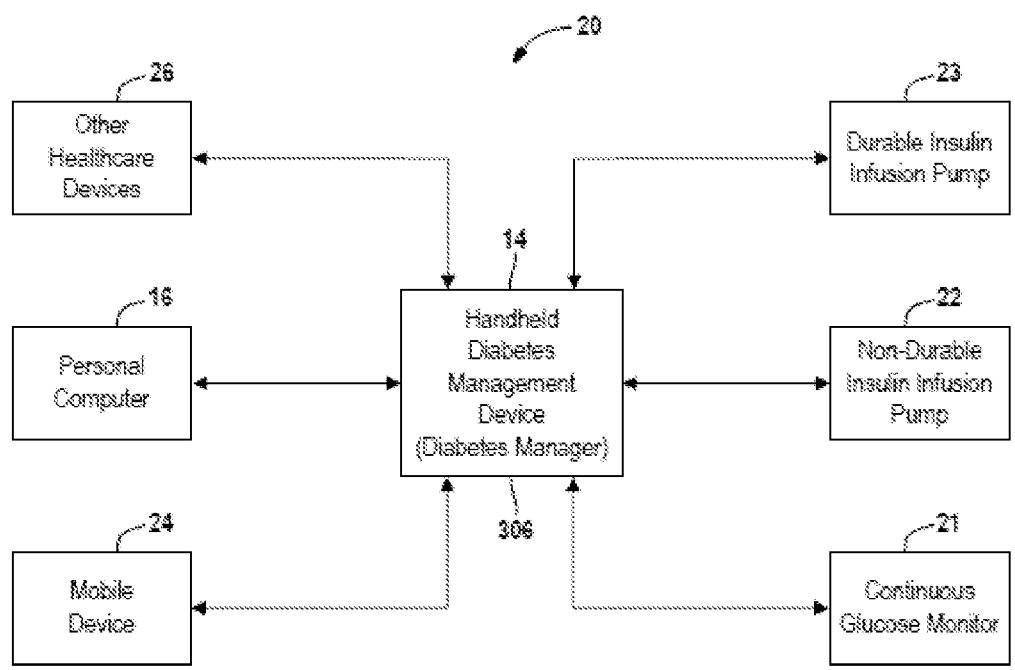
FIG. 2 is a diagram showing an exemplary diabetes management system used by patients and clinicians to manage diabetes.

An exemplary diabetes management system 20 for use by the patient 10 and the clinician 12 is depicted in FIG. 2. The diabetes management system 20 may include one or more of the following devices: the diabetes manager 14, a continuous glucose monitor (CGM) 21, a durable or non-durable insulin pump 22 or 23, a mobile device 24, the PC 16 with the diabetes analysis software, and/or other types of healthcare devices 26. In an exemplary arrangement, the diabetes manager 14 is configured as a system hub and communicates with the devices of the diabetes management system 20. Alternatively, the insulin pump 23 or the mobile device 24 can serve as the system hub. In other arrangements, the devices communicate directly with each other without the use of a system hub. Communication between the devices in the diabetes management system 20 can be performed using wireless interfaces (e.g., Bluetooth) and/or wireline interfaces (e.g., USB). Communication protocols used by these devices can include, for example, protocols compliant with the IEEE 11073 standard as extended using guidelines provided by Continua® Health Alliance Design Guidelines.

The diabetes manager 14 can receive blood glucose readings from one or more sources (e.g., from the CGM 21). For example, the CGM 21 continuously measures the blood glucose level of the patient 10. The CGM 21 periodically communicates the blood glucose level to the diabetes manager 14. The diabetes manager 14 and the CGM 21 communicate wirelessly, for example, using a proprietary Gazell wireless protocol developed by Nordic Semiconductor, Inc.

Additionally, the diabetes manager 14 includes a blood glucose meter (BGM) and a port that communicates with the BGM (not shown). The port can receive a blood glucose measurement strip. The patient 10 deposits a sample of blood or other bodily fluid on the blood glucose measurement strip. The BGM analyzes the sample and measures the blood glucose level in the sample. The blood glucose level measured from the sample and/or the blood glucose level read by the CGM 21 can be used to determine the amount of insulin to be administered to the patient 10. To create repeatable objective evidence assessing glycemic control that can be used to make a medical assessment or optimization, diabetes manager 14 may execute one or more controlled blood glucose testing regimens, known as structured tests. The diabetes manager 14 may also be configured with software programs (i.e., bolus advisor) that compute a recommend insulin dosages and/or adjustments thereto.

The diabetes manager 14 can communicate with the insulin pump 22 or 23. The insulin pump 22 or 23 can be configured to receive instructions from the diabetes manager 14 to deliver a predetermined amount of insulin to the patient 10. Additionally, the insulin pump 22 or 23 can receive other information including meal and/or exercise schedules of the patient 10. The insulin pump 22 or 23 may include a bolus advisor that can recommend an amount of insulin to administer based on the additional information.

The insulin pump 22 or 23 can also communicate data to the diabetes manager 14. The data can include amounts of insulin delivered to the patient 10, corresponding times of delivery, and pump status. The diabetes manager 14 and the insulin pump 22 or 23 can communicate using a wireless communication protocol such as Bluetooth. Other wireless or wired communication protocols can also be used.

In addition, the diabetes manager 14 can communicate with the other healthcare devices 26. For example, the other healthcare devices 26 can include a blood pressure meter, a weight scale, a pedometer, a fingertip pulse oximeter, a thermometer, a smart insulin pen, etc. The other healthcare devices 26 obtain and communicate personal health information of the patient 10 to the diabetes manager 14 through wireless, USB, or other interfaces. The other healthcare devices 26 may use communication protocols compliant with ISO/IEEE 11073. The diabetes manager 14 can communicate with the other healthcare devices 26 using interfaces including
Bluetooth, USB, etc. Further, the devices of the diabetes management system 20 can communicate with each other via the diabetes manager 14.

The diabetes manager 14 can also communicate with the PC 16. Diabetes management software running on the PC 16 includes an analyzer- configurator that stores configuration information of the devices of the diabetes management system 20. The analyzer retrieves data from the diabetes manager 14, stores the data in a database, and outputs analysis results through standard web pages or computer screens in non-web based applications. The analyzer may further calculate insulin dosages for the patient based the patient's data and/or adjustments thereto as will be further described below. The configurator has a database to store configuration information of the diabetes manager 14 and the other devices. The configurator can communicate with users through standard web or computer screens in non-web applications. The configurator transmits user-approved configurations to the devices of the diabetes management system 20. Accu-Chek 360® Diabetes Management System is an example of a commercially available diabetes management software product although other products also fall within the scope of this disclosure.

The diabetes manager 14 can communicate with the mobile device 24 using, for example, Bluetooth. The mobile device 24 may include a cellular phone, a pager, or a personal digital assistant (PDA). The diabetes manager 14 can send messages to an external network through the mobile device 24. The mobile device 24 can transmit messages to the external network upon receiving requests from the diabetes manager 14.

Figure 3:
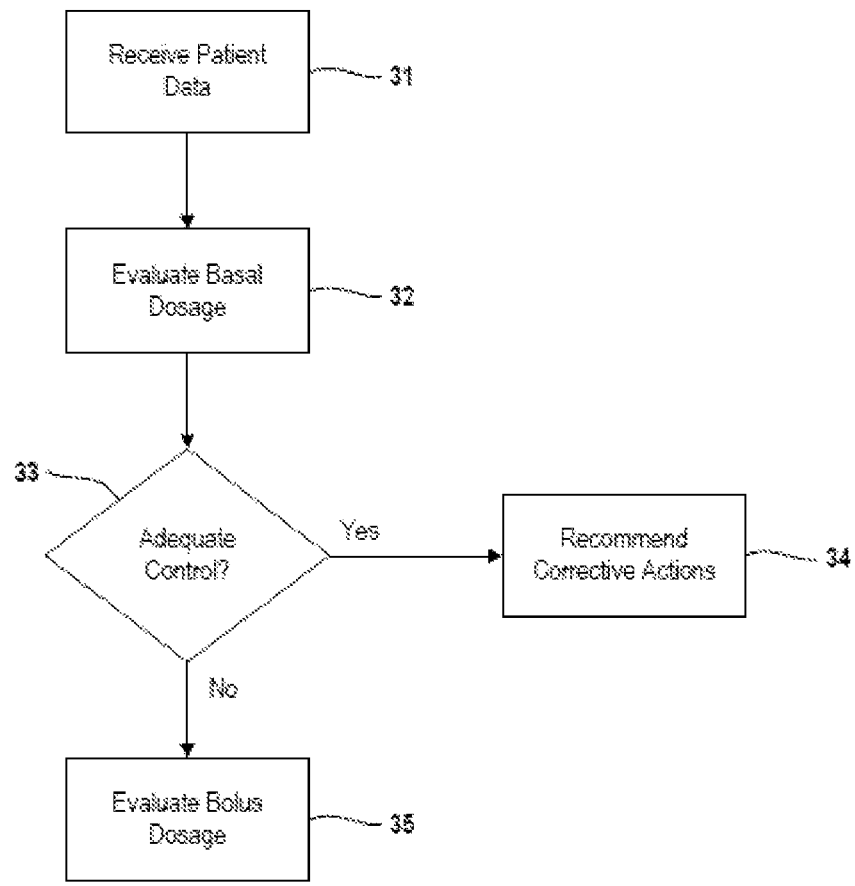
FIG. 3 is a flowchart providing an overview of a computer-implemented method for recommending insulin dosage adjustments for patients having diabetes.

FIG. 3 provides an overview of a computer-implemented method for recommending insulin dosage adjustments for patients having diabetes. In an exemplary embodiment, the methods set forth below are implemented as part of a therapy advice tool residing on the PC 16. The therapy advice tool operates generally to analyze a patient's data, including blood glucose measures, and provide reports regarding the same. It is envisioned that the therapy advice tool may also be integrated into other system devices, including the diabetes manager 14.

Patient data pertaining to the patient is received at 31 by the therapy advice tool. Patient data may be retrieved from a data store on or external to the computer device (e.g., from a glucose meter). In some cases, the data may span a relatively long period of time (e.g., more than two months). During this time, therapy changes may have been made or the general quality of glycemic control may have changed. In order to make therapy decisions on the most relevant data, restrictions may be implemented as to what data is being used for analysis. In some embodiments, the therapy advice tool may impose a predefined window of time (e.g., two weeks). In other embodiments, the therapy advice tool may provide a limit which may be overridden by the user. Presenting data to the user, such as the weekly mean and standard deviation of blood glucose readings, may help to identify which time periods of control are most representative of the current state of therapy.

First priority is to optimize basal insulin dosages for a patient. In people without diabetes, a steady amount of insulin is released into the bloodstream throughout the day. This insulin helps control blood sugar between meals and during sleep and is typically referred to as basal insulin. Thus, basal insulin is a type of slow acting insulin prescribed to control blood sugar through the day. On the other hand, bolus insulin is a type of fast acting insulin that gives the body a quick rise in insulin levels to deal with elevated blood glucose levels commonly caused, for example, by meals.

Basal insulin dosages are evaluated at 32, for example, in the manner further described below in relation to FIG. 4. A determination is then made at 33 as to whether the basal dosage is providing adequate control of blood sugar in the patient. In the exemplary embodiment, the therapy advice tool proceeds at 35 with an evaluation of the bolus insulin dosages only when the basal insulin dosage is resulting in adequate control of blood sugar in the patient. When the basal insulin dosage is inadequate to control the blood sugar in the patient, the therapy advice tool recommends at 34 some type of corrective action. For example, the therapy advice tool may recommend adjustments to the patient's basal insulin dosage. In this way, basal dosages can be optimized for the patient before evaluating the prescribed bolus insulin therapy. In other embodiments, the therapy advice tool may evaluate bolus insulin dosages even when the basal dosages are resulting in inadequate control of the blood sugar in the patient.

An exemplary process for evaluating basal insulin dosages is further described in relation to FIG. 4. Accurately dosed basal insulin should maintain stable blood glucose levels over periods of fasting at normal metabolic rate. The most telling of these fasting periods is the fasting overnight between the last meal of the day and waking up the next day. Pre-meal fasting values are also an important indicator of basal insulin action. Although pre-meal fasting values occur after a previous meal bolus, the time between meals may be sufficient to reflect the gradual change in blood glucose that might occur if basal insulin is not optimized. Accordingly, the evaluation process begins by identifying suitable fasting periods at 41 from the patient's data for subsequent analysis. In one embodiment, suitable fasting periods include a starting blood glucose measure taken proximate to a start of the fasting period, an ending blood glucose measure taken proximate to an end of the fasting period and one or more intermediate blood glucose measures taken between the starting blood glucose measure and the ending blood glucose measure. Suitable fasting periods may also exceed a minimum duration. Fasting periods not meeting the specified criteria are discarded from subsequent analysis. In some embodiments, fasting periods are further grouped before proceeding with the analysis. For instance, the user may elect to analyze overnight fasting periods in lieu of pre-meal fasting periods or vice versa.

Fasting values are an important indicator of basal insulin accuracy, but there are many factors that complicate assessments based on fasting blood glucose. For instance, a patient may have optimized basal insulin, but still experience consistently high blood glucose in the morning if they have consistently high blood glucose at bedtime. It is not uncommon that a patient may have high blood glucose at bedtime, have a bedtime snack, and administer both carb-covering and correction bolus insulin. In this case, the waking blood glucose is influenced by the basal insulin, carb-covering insulin, and the correction insulin. Also, there is no indication of the trajectory of blood glucose during the night; the blood glucose might stay high all night or begin rising in the early morning as in the 'Dawn Phenomenon'. The strongest assessment of basal insulin is possible when these interfering factors are minimized; therefore obtaining blood glucose data in accordance with a structure testing (or structured collection procedure) as a baseline for adjustments is preferred. Accordingly, a determination is made at 42 as to whether data associated with a suitable fasting period was acquired in accordance with a structured test.

Three exemplary structured tests for acquiring blood glucose data during a fasting period are as follows. In an overnight test, patient is required to fast prior to bedtime and their blood glucose must be within a target range at bedtime. Blood glucose measures are then obtained at period intervals through the night, for example, 4 and 8 hours after bedtime. In one type of half-day test, the patient is instructed to skip breakfast and then take blood glucose measures periodically thereafter (e.g., every 1-2 hours for 8 hours). In another type of half-day test, the patient is instructed to skip lunch and then take blood glucose measures periodically thereafter. Other types of structured tests for acquiring blood glucose data during a fasting period are also contemplated by this disclosure. In any case, these types of tests pose a burden by requiring skipped or zero-carbohydrate meals during the day. Additionally, these tests reflect only one day's history, while actual basal requirements are likely to fluctuate across days. Thus, these types of tests seem most logical to be performed as a limited, baseline-establishing practice, putting the basal rate in the correct "ballpark" for the representative test day. If some reasonable certainty exists that basal insulin is within a few units from the optimized dose, then conclusions may reasonably be drawn from analyzing aggregated unstructured blood glucose data from the patient.

Blood glucose data acquired in accordance with structured testing is analyzed at 43 to ensure that it is suitable for use by the therapy advice tool. For example, the therapy advice tool may require that blood glucose data associated with a given fasting period includes at least three measures: a starting blood glucose measure taken proximate to a start of the fasting period, an ending blood glucose measure taken proximate to an end of the fasting period and at least one intermediate blood glucose measure taken between the starting blood glucose measure and the ending blood glucose measure. Since different structured test procedures may procure more or less blood glucose measures, data from each structured test may be analyzed in relation to criteria defined by the therapy advice tool.

For each fasting period having acceptable blood glucose measures associated therewith, the effectiveness of the basal insulin dosages is evaluated at 44. Specifically, this evaluation answers the question: did the patient's blood glucose values remain stable throughout the measurement period? In an exemplary embodiment, the blood glucose is deemed stable if all of the blood glucose measures or some portion thereof (e.g., 90%) associated with the structured test did not rise more than 15 mg/dL and did not fall more than 30 mg/dL from the starting blood glucose measure although other types of stability criteria are contemplated by this disclosure. Additional metrics may be used to evaluate stability of blood glucose measures acquired from multiple structured tests.

When the blood glucose values are deemed stable according to structured testing, the therapy advice tool can recommend maintaining the current basal insulin dosage as indicated at 45. Additionally or alternatively, the therapy advice tool can proceed with an evaluation of the bolus insulin therapy as indicated at 46. On the other hand, when the blood glucose values are deemed unstable, the therapy advice tool can recommend different corrective actions to the patient or the patient's healthcare provider. For example, the therapy advice tool may recommend an adjustment to the basal insulin dosage as indicated at 49. In one embodiment, the therapy advice tool can recommend increasing the insulin dosage when the blood glucose values are above the target range and decreasing the insulin dosage when the blood glucose values are below the target range. Additionally or alternatively, the therapy advice tool may recommend performing another structured test (either same or different test) at 50 to further evaluate the prescribed basal therapy.

With continued reference to FIG. 4, when blood glucose data acquired in accordance with a structured test is unavailable, the evaluation of basal insulin dosages is based on the unstructured blood glucose data (i.e., blood glucose measures acquired independent from a structured test) as indicated at 51. Blood glucose values that are sufficiently removed from any prior meals are associated with a fasting period. For each identified fasting period, a determination is made at 52 as to the effectiveness of the basal insulin dosage during the corresponding fasting period. In an exemplary embodiment, the effectiveness of the basal insulin is expressed as a basal outcome in relation to a target range of blood glucose values, where the target range may be defined in accordance with a particular medical standard or tailored to the particular patient. That is, the ending blood glucose measure is compared to the target range and classified as being either above the target range, in the target range or below the target range. Evaluating the effectiveness of basal insulin may include other techniques such as comparing an average of the blood glucose measures to the target range or classifying the fasting period as above or below if any one measure falls above or below the target range. From the individual basal outcomes associated with each fasting period, a determination is then made as to whether one of the basal outcomes is predominant amongst the identified fasting periods. In an exemplary embodiment, a percentage for each group of basal outcome is computed in relation to the total number of identified fasting periods. In other words, a percentage is computed for basal outcomes that are above the target range, basal outcomes that in the target range and basal outcomes that are below the target range. If the percentage of any one group of basal outcome exceeds a predefined threshold (e.g., 50%), then that group of basal outcome is deemed to be predominant amongst the outcomes. Other criteria for evaluating effectiveness of basal insulin also fall within the scope of this disclosure.

When the basal insulin dosage is deemed to be effective for the patient, the therapy advice tool can recommend maintaining the current basal insulin dosage as indicated at 53 and/or proceed with the evaluation of the bolus insulin therapy as indicated at 54. On the other hand, when the basal insulin dosage is deemed ineffective, the therapy advice tool can recommend different corrective actions to the patient or the patient's healthcare provider. For example, the therapy advice tool may recommend an adjustment to the basal insulin dosage as indicated at 56. Additionally or alternatively, the therapy advice tool may recommend performing a structured test at 55 to further evaluate the prescribed basal therapy.

In a simplified embodiment, the therapy advice tool can recommend increasing the insulin dosage when the blood glucose values are above the target range and decreasing the insulin dosage when the blood glucose values are below the target range. In a more robust embodiment, a recommendation to increase or decrease insulin dosages accounts for both the frequency and severity of blood glucose measures falling outside the target range. To formulate the recommendation, an outcome is determined first for each blood glucose measure. Each outcome may be expressed in relation to a target range of blood glucose values, where the target range may be defined in accordance with a particular medical standard or tailored to the particular patient. That is, the blood glucose measure is compared to the target range and classified as being either above the target range, in the target range or below the target range.

In an exemplary embodiment, severity of abnormal blood glucose may be quantified by mathematically transforming blood glucose values. The output of this transformation may be termed "glycemic hazard" and may be calculated in a way derived from the transformation described by Kovatchev et. al. in "Assessment of Rick for Severe Hypoglycemia among Adults with IDDM: Validation of the Low Blood Glucose Index" Diabetes Care (1992), where Kovatchev's equation is express as $$\text{Transformed } bG = 1.509 \times [(\log bG)1.026 - 5.381]$$

Figure 5A:
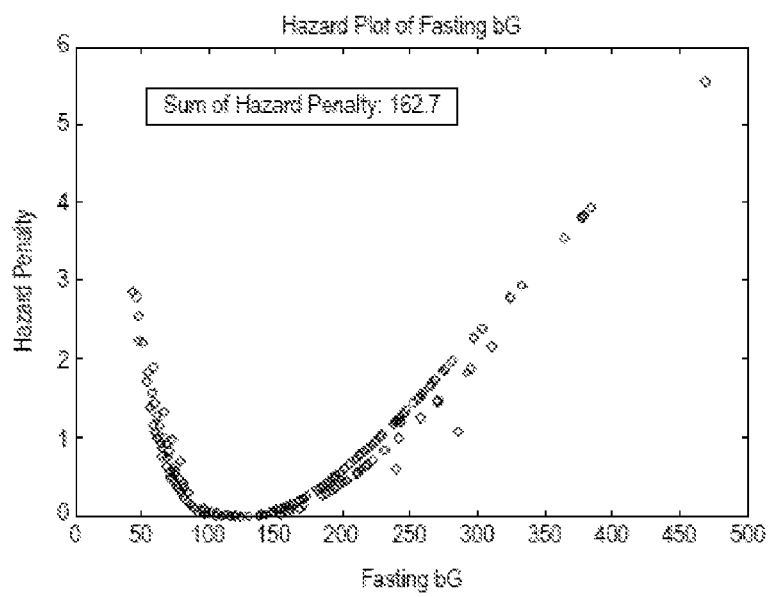
FIGS. 5A and 5B are hazard plots of a patient's blood glucose measures during fasting and shifted by +10 mg/dL, respectively.
Figure 5B:
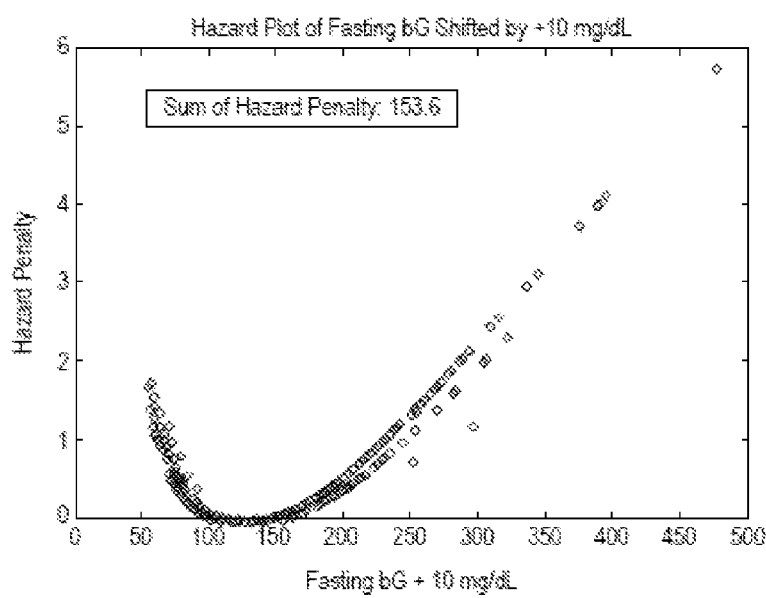

This equation is then modified to ensure that all blood glucose values within the target range have a transformed value of zero. Next, a severity penalty is assigned to each out-of-range blood glucose value. In range blood glucose values are given a penalty of zero. Penalties values are summed such that the sum of the penalties represents the current state of overall glycemic hazard. To simulate the effect of changes in insulin dosages, 5 mg/dL may be added (or subtracted) from each blood glucose measure. Severity penalties are re-assigned to the adjusted blood glucose values and the sum of penalties in each group is re-computed. This simulates what the effect would be of increasing or decreasing the mean blood glucose value. The process may be repeated several times by adding or subtracting different increments, for example, +10, +15, −5, −10 and −15 mg/dL. The scenario having the lowest sum is preferred. A recommendation can then be formulated based on whether the minimized sum was achieved by increasing or decreasing the blood glucose value. FIGS. 5A and 5B are plots of penalty values in relation to blood glucose values. In FIG. 5B, the blood glucose values were shifted by +10 mg/dL. In this example, while the number of above-range values is increased, hypoglycemia represents the greater hazard when severity of the measures is considered. Other techniques for formulating a recommendation for an adjustment to an insulin dosage also fall within the broader aspects of this disclosure.

Figure 6:
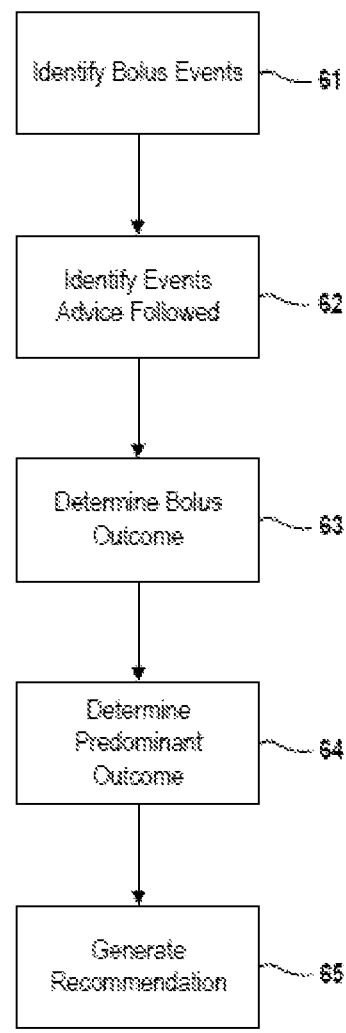
FIG. 6 is a flowchart illustrating a method for recommending bolus insulin dosage adjustments for patients.

Once the patient has achieved a reasonable certainty that basal insulin therapy is appropriate, the evaluation may proceed to bolus insulin therapy. Rapid-acting insulin is delivered as a "bolus" to lower blood glucose concentrations and to compensate for carbohydrates consumed in meals. An overview of a computer-implemented method for recommending insulin dosage adjustments to bolus insulin therapy is provided in FIG. 6.

First, suitable bolus events are identified at 61 for analysis. Suitable bolus events may include a bolus dosage of insulin recommended to the patient, an amount of insulin administered to the patient in response to the recommended bolus dosage, and a blood glucose measure taken during an acting time of the administered insulin. Suitable bolus events are extracted from patient data in a specified time period as indicated in step 31 of FIG. 3.

Bolus events are further partitioned at 62 into a first subset of bolus events in which the patient followed the recommended bolus dosage and a second subset of bolus events in which the patient did not follow the recommended bolus dosage. Patients are deemed to have followed the recommendation when the recommend bolus dosage is substantially equivalent to the amount of insulin administered to the patient in response to the recommendation. This step helps to determine whether problem in glycemic control come from therapy non-adherence vs. inappropriate therapy setting as further explained below.

Next, a bolus outcome is determined at 63 for each bolus event in the first subset of bolus events. In an exemplary embodiment, a bolus outcome is expressed in relation to a target range of blood glucose values, where the target range may be defined in accordance with a particular medical standard or tailored to the particular patient. More specifically, the blood glucose measure associated with the bolus event is compared to the target range and classified as being either above the target range, in the target range or below the target range.

From the individual bolus outcomes, a determination is then made at 64 as to whether one of the outcomes is predominant. In an exemplary embodiment, a percentage for each type of bolus outcome is computed in relation to the total number of bolus events in the first subset of bolus events. In other words, a percentage is computed for bolus outcomes that are above the target range, bolus outcomes that in the target range and bolus outcomes that are below the target range. If the percentage of any one type of bolus outcome exceeds a predefined threshold (e.g., 50%), then that type of bolus outcome is deemed to be predominant amongst the outcomes. Other techniques for determining predominance are also contemplated by this disclosure.

Lastly, a recommendation pertaining to the patient's insulin dosage is generated at 65 in response to a determination that one of the bolus outcomes is predominant. In a simple embodiment, the therapy advice tool may make qualitative recommendations. For example, the therapy advice tool may recommend maintaining the current insulin dosage when the bolus outcomes are predominantly in the target range, recommend increasing insulin dosage when the bolus outcomes are predominantly above the target range, and recommend decreasing insulin dosage when the bolus outcomes are predominantly below the target range. More robust embodiments may include quantitative amounts for adjusting insulin dosages.

Figure 7:
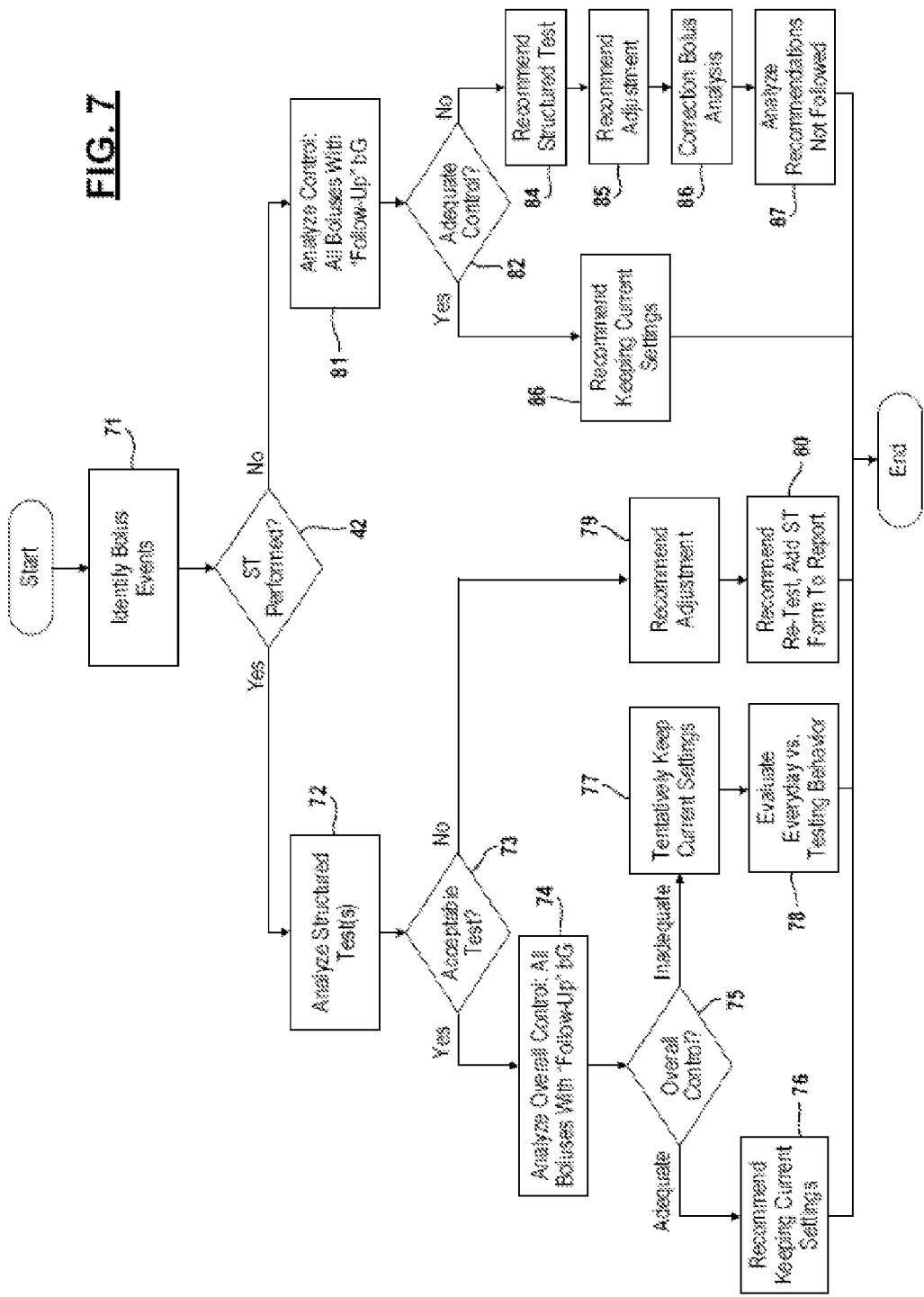
FIG. 7 is a flowchart depicting an exemplary process for evaluating bolus insulin dosages.

FIG. 7 depicts an exemplary embodiment for evaluating bolus insulin dosages. The evaluation process begins at 71 by identifying suitable bolus events in the manner described above. Insulin-to-carbohydrate ratios (I:CHO) and insulin sensitivity factors (ISF) for a patient may be set differently for different time periods (i.e., time blocks) during the day. This allows bolus calculations to reflect circadian fluctuations in metabolism. Bolus events falling into different time block are preferably assessed separately. In one embodiment, the user specifies a time block of interest (e.g., 8 am-noon). Suitable bolus events falling within the specified time block are grouped together and the evaluation proceeds for suitable bolus events in the specified time block proceeds. Thus, subsequent therapy advice can then be provided on a block-by-block basis. In other embodiments, the evaluation proceeds on the basis of all suitable bolus events.

As in the case of basal insulin, several structured testing options exist to help optimize bolus insulin settings, including I:CHO and ISF. Suitable bolus events may be analyzed and partitioned at 72 depending upon the type of structured test they were acquired from. A first type of structured test may isolate the effect of insulin on the I:CHO setting; whereas, a second type of structured test may isolate the effect of insulin of the ISF setting. In the first type of structured test, a carbohydrate-covering bolus is given according to the carbohydrate content of a particular meal, where the blood glucose is within the target range before the meal. Blood glucose is then measured at one, two and three hours following the bolus. When the blood glucose measure returns to the target range, the I:CHO setting is confirmed as being correct by the first type of structured test. In a second type of structured test, a correction bolus is given when the blood glucose is over 200 mg/dl. Blood glucose is then measured at one, two and three hours after the bolus is given without any food being consumed by the patient during the three hour period. When the blood glucose measure returns to the target range, the ISF setting is confirmed as being correct by the second type of structured test. Accordingly, bolus events derived from one type of structured test are preferably analyzed independently from the bolus events derived from the other type of structured test. Other types of structured testing which help to isolate the effect of the bolus insulin dosage are contemplated by this disclosure.

Structured test results are analyzed at 72 to ensure that the results are suitable for use by the therapy advice tool. Different types of structured tests may have different criteria. For example, a given test may require that blood glucose measures be taken at three or more specified times after a bolus. When each criterion has been met, the structured test is deemed to be acceptable at 73. In one embodiment, recommendations proceed on the basis of blood glucose measures obtained only from structured test deemed acceptable. In other embodiments, recommendations may be based on bolus events acquired in accordance with a structured test as well as bolus events acquired independent from a structured test.

Bolus events are analyzed at 74 to determine the effectiveness of the bolus insulin dosages. In an exemplary embodiment, the analysis is performed only on data where the patient adhered to the recommendations. If the patient does not follow the recommendations, then the resulting therapy advice is not meaningful. Patients are deemed to have followed the recommendation when the recommend bolus dosage is substantially equivalent to the amount of insulin administered to the patient. Conversely, a recommendation is viewed as not being followed when either the amount of insulin administered differs from the recommendation or the recommendation function (i.e., bolus calculator) was not used by the patient before administering insulin. For bolus events where the patient followed the recommendation, an outcome is determined for each bolus event. In the exemplary embodiment, the bolus outcome is expressed in relation to a target range of blood glucose values, where the target range may be defined in accordance with a particular medical standard or tailored to the particular patient. That is, the blood glucose measure associated with the bolus event is compared to the target range and classified as being either in the target range or outside the target range. A determination is made at 75 as to whether the administered insulin provided adequate control. When the percentage of bolus outcomes classified as being in range exceeds a predefined threshold (e.g., 70%), the bolus insulin therapy, including any underlying settings such as I:CHO and ISF, are deemed to be effective. In this case, the therapy advice tool recommends maintaining the current bolus insulin dosage as indicated at 76. The bolus insulin therapy is deemed ineffective when the percentage of bolus outcomes resulting in range is less than the predefined threshold. Because the therapy remains ineffective even within a structured environment, the therapy advice tool recommends maintaining the current bolus insulin dosage at 77. Additionally, the therapy advice tool at 78 recommends exploring with the patient different behavior which may be leading to the ineffective therapy.

On the other hand, when test criterion has not been met and the structured test is deemed at 73 to be unacceptable, the therapy advice tool can recommend different corrective actions to the patient or the patient's healthcare provider. For example, the therapy advice tool may recommend an adjustment to the basal insulin dosage as indicated at 79. Additionally or alternatively, the therapy advice tool may recommend performing the same or different structured test at 80 to further evaluate the prescribed basal therapy.

When bolus events acquired in accordance with a structured test are unavailable, the evaluation of bolus insulin dosages is based on unstructured blood glucose data (i.e., blood glucose measures acquired independent from a structured test). Bolus events are again analyzed at 81 to determine the effectiveness of the bolus insulin dosages. The bolus event may be analyzed in the same manner as described above in relation to step 74. A determination is made at 82 as to whether the administered insulin provided adequate control. In this case, the therapy advice tool recommends maintaining the current basal insulin dosage as indicated at 83.

On the other hand, bolus insulin therapy is deemed ineffective when the percentage of bolus outcomes resulting in range is less than the predefined threshold. In this case, the therapy advice can recommend one or more different corrective actions. For example, the therapy advice tool can recommend performing a structured test at 84 to further evaluate the bolus insulin therapy. In another example, the therapy advice tool may recommend an adjustment to the basal insulin dosage as indicated at 85. Different techniques for formulating a recommendation may be employed, including those set forth above in relation to step 49 of FIG. 4. In yet another example, the bolus events may be analyzed at 86 to independently assess either I:CHO or ISF. Correction only bolus event are those administered when blood glucose needs to be lowered but no meal is being consumed. These events offer an opportunity to assess ISF independently of I:CHO. If the outcomes of correction-only boluses are accurate, then ISF may be considered to be optimized. In the case that ISF is optimized but overall bolus outcomes are not optimized, the therapy advice tool may, for example, focus efforts on optimizing meal dosing by modifying I:CHO.

In some instances, a patient's intuition and/or experience may serve as a better estimator of bolus insulin than a computer-implemented bolus recommendation function. To account for this possibility, bolus events where the patient did not follow a recommendation are also analyzed as indicated at 87. In an exemplary embodiment, an outcome is determined for each bolus event in this grouping, where the bolus outcome is expressed in relation to a target range of blood glucose values. That is, the blood glucose measure associated with the bolus event is compared to the target range and classified as being either in the target range or outside the target range. When the percentage of bolus outcomes classified as in range exceeds a predefined threshold (e.g., 70%), the patient's intuition is deemed effective and may serve as a basis for providing a recommended adjustment.

Bolus calculation is performed according to a linear equation with I:CHO and ISF as coefficients. In an exemplary embodiment, a basic bolus dose calculation is carried out according to $$\text{Insulin Dosed} = \text{I:CHO} \times \text{CHO intake} + \text{ISF} \times (\text{BG} - \text{target BG})$$

In more robust embodiments, the bolus calculator may consider "active insulin" or "insulin on board". When considering that CHO intake and BG are variables while I:CHO, ISF, and target BG are all fixed parameters, the equation reduces to the form ans=Ax+By+C. Using linear regression solves for A and B, yielding the best fit values for I:CHO and ISF. Accordingly, through linear regression, I:CHO and ISF that are closest to producing the same amount of insulin in the group of bolus events where the patient did not follow the recommendation. How consistently these patient intuition-derived "rules" were applied can be determined from $R^2$, representing goodness of fit for these ratios. The therapy advice tool interprets this analysis, indicating to the user whether changing the prescribed bolus calculation rules to match the patient's intuitive behavior or simply following the prescribed rules more consistently is the most appropriate response.

Recommendations generated by the therapy advice tool may be communicated to the patient and/or the health care provider in a variety of manners. In one exemplary embodiment, recommendations are conveyed using a report as shown in FIG. 8. Recommendations set forth on the report will depend on the analysis as described above. Other formats for the report as well as medium for communicating the report are contemplated by this disclosure.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The present disclosure is well suited to a wide variety of computer network systems over numerous topologies. Within this field, the configuration and management of large networks comprise storage devices and computers that are communicatively coupled to dissimilar computers and storage devices over a network, such as the Internet.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same can also be varied in many ways. Such variations are not to be regarded as a departure from the disclosure, and all such modifications are intended to be included within the scope of the disclosure.

What is claimed is:

1. A non-transitory processor-readable medium storing instructions that, when executed by a processor, cause the processor to perform operations, comprising:
   receiving patient data pertaining to diabetes care of a patient;

identifying a plurality of bolus events from the patient data, each of the identified bolus events having associated therewith a bolus dosage of insulin recommended to the patient, an amount of insulin administered to the patient in response to the recommended bolus dosage, and a glucose measure taken during an acting time of the administered insulin;

grouping, from the plurality of bolus events, bolus events having a recommended bolus dosage that differs from the amount of administered insulin into a first subset of bolus events;

determining a bolus outcome for each of the bolus events in the first subset of bolus events, where the bolus outcome is expressed in relation to a target range of glucose values and is selected from a category including above the target range, in the target range and below the target range;

calculating a percentage of bolus outcomes in each category of bolus outcomes in relation to a number of bolus events in the first subset of bolus events; and generating a recommendation pertaining to insulin dosage for the patient using the percentage of bolus outcomes in each category, wherein the recommendation indicates changing a patient's insulin dosages according to those bolus events having a recommended bolus dosage that differed from the amount of administered insulin and determined to have a bolus outcome in the target range.

2. A computer-implemented method for recommending insulin dosage adjustments for a patient having diabetes, comprising:

receiving patient data pertaining to diabetes care of the patient;

identifying a plurality of bolus events from the patient data, each of the identified bolus events having associated therewith a bolus dosage of insulin recommended to the patient, an amount of insulin administered to the patient in response to the recommended bolus dosage, and a glucose measure taken during an acting time of the administered insulin;

grouping, from the plurality of bolus events, bolus events having a recommended bolus dosage substantially equivalent to the amount of administered insulin into a first subset of bolus events;

grouping, from the plurality of bolus events, bolus events having a recommended bolus dosage that differs from the amount of administered insulin, into a second subset of bolus events;

determining a bolus outcome for each of the bolus events in the second subset of bolus events, where the bolus outcome is expressed in relation to a target range of glucose values and is selected from a category including above the target range, in the target range and below the target range;

determining whether bolus outcomes in the category of in the target range is a majority of bolus outcomes for bolus events in the second subset of bolus events; and generating a recommendation pertaining to insulin dosage for the patient in response to a determination that bolus outcomes in the category of in the target range is a majority of bolus outcomes for bolus events in the second subset of bolus events, wherein the recommendation indicates changing a patient's insulin dosages according to those bolus events having a recommended bolus dosage that differed from the amount of administered insulin and determined to have a bolus outcome in the target range, and wherein the steps of identifying, grouping and determining are executed by a processor of a computing device.

3. The method of claim 2 wherein the step of determining whether the bolus outcomes is predominant further comprises calculating a percentage of bolus outcomes in the target range in relation to a number of bolus events in the second subset of bolus events and deeming the bolus outcomes are predominant when the percentage of bolus outcomes exceeds a predefined threshold.

4. The method of claim 2 wherein generating a recommendation further comprises calculating coefficients of a linear equation using the bolus events in the second subset of bolus events, where the linear equation computes the bolus dosage of insulin recommended to the patient.

5. A computer-implemented method for recommending insulin dosage adjustments for a patient having diabetes, comprising:

receiving patient data pertaining to diabetes care of the patient;

identifying a plurality of fasting periods from the patient data, each of the identified fasting periods having associated therewith at least one glucose measure;

determining a basal outcome for each of the fasting periods in the plurality of fasting periods, where the basal outcome is expressed in relation to a target range of glucose values and selected from a group including above the target range, in the target range and below the target range;

determining whether one of the basal outcomes is predominant amongst the fasting periods in the plurality of fasting periods; and evaluating a bolus dosage of insulin prescribed for the patient in response to a determination that basal outcomes for the patient are predominantly in the target range of glucose values, wherein evaluating a bolus dosage includes:

identifying a plurality of bolus events from the patient data, each of the identified bolus events having associated therewith a bolus dosage of insulin recommended to the patient, an amount of insulin administered to the patient in response to the recommended bolus dosage, and a glucose measure taken during an acting time of the administered insulin;

grouping, from the plurality of bolus events, bolus events having a recommended bolus dosage that differs from the amount of administered insulin into a first subset of bolus events;

determining a bolus outcome for each of the bolus events in the first subset of bolus events, where the bolus outcome is expressed in relation to a target range of glucose values and is selected from a category including above the target range, in the target range and below the target range;

determining whether bolus outcomes in the category of in the target range is a majority of bolus outcomes for bolus events in the first subset of bolus events; and generating a recommendation pertaining to insulin dosage for the patient in response to a determination that bolus outcomes in the category of in the target range is a majority of bolus outcomes for bolus events in the first subset of bolus events, wherein the recommendation indicates changing a patient's insulin dosages the according to those bolus events having a recommended bolus dosage that differed from the amount of administered insulin and determined to have a bolus outcome in the target range, and wherein the steps of identifying, grouping and determining are executed by a processor of a computing device.

6. The method of claim 5 wherein the step of determining whether one of the basal outcomes is predominant further comprises calculating a percentage of basal outcomes in each grouping of basal outcomes in relation to a number of basal outcomes in the plurality of fasting periods.

7. The method of claim 6 further comprises deeming a given group of basal outcomes is predominant when the percentage of the given group of basal outcomes exceeds a predefined threshold.

8. The method of claim 5 further comprises recommending to maintain current insulin dosage in response to a determination that basal outcomes for the patient are predominantly in the target range of glucose values.

9. The method of claim 5 further comprises recommending an increase in insulin dosage in response to a determination that basal outcomes for the patient are predominantly above the target range of glucose values.

10. The method of claim 5 further comprises recommending a decrease in insulin dosage in response to a determination that basal outcomes for the patient are predominantly below the target range of glucose values.

11. The method of claim 5 further comprises recommending, in response to a determination that basal outcomes are predominantly outside the target range of glucose values, to acquire glucose measures from the patient in accordance with a structured collection procedure, where the structured collection procedure specifies timing for one or more collection events for obtaining glucose measures from the patient.

12. The method of claim 5 wherein each of the identified fasting periods having associated therewith a starting glucose measure taken proximate to a start of the fasting period, an ending glucose measure taken proximate to an end of the fasting period and at least one intermediate glucose measure taken between the starting glucose measure and the ending glucose measure.

13. The method of claim 5 further comprises adjusting the bolus dosage of insulin administered to the patient in accordance with the recommendation.

* * * * *